US008865478B2

(12) United States Patent
Juo et al.

(10) Patent No.: US 8,865,478 B2
(45) Date of Patent: Oct. 21, 2014

(54) REAGENTS, KITS AND METHODS FOR DETECTING BIOLOGICAL MOLECULES BY ENERGY TRANSFER FROM AN ACTIVATED CHEMILUMINESCENT SUBSTRATE TO AN ENERGY ACCEPTOR DYE

(75) Inventors: Rouh-Rong Juo, Allston, MA (US); John C. Voyta, Sudbury, MA (US); Brooks Edwards, Cambridge, MA (US)

(73) Assignee: Applied Biosystems LLC, Carlsbad, CA (US)

( * ) Notice: Subject to any disclaimer, the term of this patent is extended or adjusted under 35 U.S.C. 154(b) by 695 days.

(21) Appl. No.: 12/126,094

(22) Filed: May 23, 2008

(65) Prior Publication Data
US 2009/0047688 A1 Feb. 19, 2009

Related U.S. Application Data

(60) Provisional application No. 60/924,640, filed on May 23, 2007.

(51) Int. Cl.
*G01N 33/533* (2006.01)
*C12M 1/34* (2006.01)
*G01N 33/543* (2006.01)
*G01N 33/58* (2006.01)
*G01N 33/542* (2006.01)

(52) U.S. Cl.
CPC ........ *G01N 33/542* (2013.01); *G01N 33/54313* (2013.01); *G01N 33/581* (2013.01); *G01N 33/533* (2013.01)
USPC ...................................... 436/546; 435/287.2

(58) Field of Classification Search
CPC .............. G01N 33/553; G01N 33/581; G01N 33/54313; G01N 33/542
See application file for complete search history.

(56) References Cited

U.S. PATENT DOCUMENTS

| | | | |
|---|---|---|---|
| 5,071,909 A | 12/1991 | Pappin et al. | |
| 5,145,772 A | 9/1992 | Voyta et al. | |
| 5,169,788 A | 12/1992 | Chen et al. | |
| 5,451,347 A | 9/1995 | Akhavan-Tafti et al. | |
| 5,827,650 A | 10/1998 | Bronstein et al. | |
| 6,028,190 A | 2/2000 | Mathies et al. | |
| 6,335,440 B1 | 1/2002 | Lee et al. | |
| 6,849,745 B2 | 2/2005 | Lee et al. | |
| 7,169,939 B2 | 1/2007 | Lee et al. | |
| 2003/0134286 A1 | 7/2003 | Edwards et al. | |
| 2005/0026151 A1 | 2/2005 | Voyta et al. | |
| 2009/0047688 A1 | 2/2009 | Juo et al. | |
| 2010/0331543 A1* | 12/2010 | Diwu et al. .................. 546/113 |

FOREIGN PATENT DOCUMENTS

| | | |
|---|---|---|
| EP | 1542013 A1 | 6/2005 |
| JP | 2005-515469 | 5/2005 |
| KR | 20020053514 A1 | 7/2002 |
| WO | WO-2008147949 | 12/2008 |

OTHER PUBLICATIONS

De Rossi et al. Spontaneous formation of chirality in J-aggregates showing davydov splitting. Angew. Chem. Int. Ed. Engl. 1996, vol. 35, No. 7, pp. 760-763.*

(Continued)

*Primary Examiner* — Shafiqul Haq
(74) *Attorney, Agent, or Firm* — Applied Biosystems LLC

(57) ABSTRACT

Reagents, kits and methods for detecting biological molecules by energy transfer from an activated chemiluminescent substrate to an energy acceptor dye such as a J-aggregated dye are described.

10 Claims, 7 Drawing Sheets

(56) References Cited

OTHER PUBLICATIONS

Mishra et al., "Cyanines During the 1990's: A Review," Chem. Rev. 2000, 100, 1973-2011.

Von Berlepsch et al., "Effect of alcohols on J-Aggregation of a carbocyanine dye," Langmuir 2002, 7699-7705.

Harris et al., "Synthesis of Passivating, Nylon-Like Coatings Through Cross-Linking of Ultrathin Polyelectrolyte Films," J. Am. Chem. Soc., 1999, 121:1978-1979.

Patel et al., "Chemiluminescence Energy Transfer: A New Technique Applicable to the Study of Ligand-Ligand Interactions in Living Systems", Analyt. Biochem. 129:162-169 (1983).

Patel et al., "Homogeneous Immunoassay Based on Chemiluminescence Energy Transfer," Clin. Chem. 29/9, 1604-1608, 1983.

Williams et al., "A Homogeneous Assay for Biotin Based on Chemiluminescence Energy Transfer," Analyt. Biochem., 155:249-255, 1986.

Akerstrom et al., "A Physicochemical Study of Protein G, a Molecule with Unique Immunoglobulin G-Binding Properties," J. Biol. Chem., 1986, 261:10240-10247.

Molecular Probes' Cell Biology Products, 2004/2005 Catalog, 14-28, http://www.probes.com/lit/catalog/3/sections/1919.html.

Clapp, et al., "Can Luminescent Quantum Dots Be Efficient Energy Acceptors with Organic Dye Donors," J. Am Chem. Soc., vol. 127, 2005, 1242-1250.

Hildebrandt, et al., "Quantum Dots as efficient Energy Acceptors in a Time-Resolved Fluoroimmunoassay," Agnew. Chem. Int. Ed., vol. 44, 2005, 7612-7615.

Huang, et al., "A Resonance Energy Transfer between Chemiluminescent Donors and Luminescent Quantum-Dots as Acceptors (CRET)," Agnew. Chem. Int. Ed., vol. 45, 2006, 5140-5143.

Place, et al., "Stabilization of the Aggregation of Cyanine Dyes at the Molecular and Nanoscopic Level," Langmuir, vol. 16, 2000, 9042-9048.

So, et al., "Self-illuminating Quantum Dot Conjugates for in vivo Imaging," Nature Biotechnology, vol. 24, No. 3, 2006, 339-343.

Yao, et al., "Quantum Dot/Bioluminescence Resonance Energy Transfer Based Highly Sensitive Detection of Proteases," Agnew. Chem. Int. Ed., vol. 46, 2007, 4346-4349.

Extended European Search Report received in European Application No. 09180519.2 mailed Jun. 28, 2010.

Office Action received in European Application No. 09180519.2 mailed Feb. 24, 2011.

Partial European Search Report received in European Application No. 09180519.2 mailed Apr. 6, 2010.

Response to European Office Action dated Feb. 24, 2011 filed Mar. 16, 2011.

Office Action received in Chinese Application No. 200880019672.X mailed Aug. 11, 2010.

International Preliminary Report on Patentability for PCT Application No. PCT/US08/064643 mailed Nov. 24, 2009.

International Search Report for PCT Application No. PCT/US08/064643 mailed Nov. 4, 2008.

Lakowicz, J., "Principles of Fluorescence Spectroscopy", *Kluwer Academic/Plenum Publishers,* 1999, p. 388.

Hayashi, Yoko et al., "Enzyme Immunoassay of Prostaglandin F2a", *Biochimica et Biophysica Acta,* 1981, 661-668.

Place, I. et al., "Stabilization of the Aggregation of Cyanine Dyes at the Molecular and Nanoscopic Level", *Langmuir,* vol. 16, Center for Photoinduced Charge Transfer, University of Rochester, Rochester, New York 14627, 2000, pp. 9042-9048.

\* cited by examiner

REAGENTS, KITS AND METHODS FOR DETECTING BIOLOGICAL MOLECULES BY ENERGY TRANSFER FROM AN ACTIVATED CHEMILUMINESCENT SUBSTRATE TO AN ENERGY ACCEPTOR DYE

This application claims the benefit of Provisional U.S. Patent Application Ser. No. 60/924,640, filed on May 23, 2007, which is incorporated by reference herein in its entirety.

The section headings used herein are for organizational purposes only and should not be construed as limiting the subject matter described herein in any way.

FIELD

This application relates generally to reagents, kits and methods for detecting biological molecules in a sample.

INTRODUCTION

Bioassay customers are increasingly adopting homogeneous assay formats in lieu of heterogeneous assays, preferring simpler, fewer steps (e.g., no separation step) which translate into less labor and faster time to obtaining results.

As described herein, sensitive homogeneous bioassays can be conducted on a support surface, wherein localized enzyme turnover generates localized chemiexcitation of an acceptor dye layer (e.g., a J-aggregate dye) on the support which correlates to nearby captured analyte detection. The support assemblies can be used as sensitive bioassay supports for chemiluminescent homogeneous enzyme-labeled bioassays in chip formats and solution assays. The assay design can also accommodate mixes of different support assemblies, providing multiple assays in a homogeneous assay format. The capability of wavelength-shifting the luminescent signal away from auto-fluorescence bands, and initiating the signal from chemiexcitation, can provide lower background, increased signal to noise, increased dynamic range, increased detection sensitivities, and significantly simplified instrument readout.

SUMMARY

An article of manufacture is provided which comprises;
a support having a surface;
a chemiluminescent enhancing material on the surface of the support;
an energy acceptor dye on the surface of the support; and
one or more biomolecular probes on the surface of the support.

A kit for detecting analyte in a sample is also provided which comprises:
an article of manufacture as set forth above, wherein the one or more biomolecular probes includes a probe that is capable of binding to the analyte or, when the analyte is present, which binds to the analyte;
a chemiluminescent substrate; and
optionally, an enzyme-labeled biomolecule or an enzyme-labeled analyte. The enzyme-labeled biomolecule can bind to the analyte when the analyte is bound to the surface-bound probe. The enzyme-labeled analyte can compete with unlabeled analyte in the sample for binding to the surface-bound probe.

A method for detecting analyte in a sample is also provided which comprises:
contacting the sample with an article of manufacture as set forth above, wherein the one or more biomolecular probes comprises a probe which is capable of binding to the analyte;
allowing analyte in the sample to bind to the probe; wherein: (a) the analyte is an enzyme; (b) the analyte is labeled with an enzyme; (c) the support surface is contacted with an enzyme-labeled biomolecule which binds to the analyte; or (d) the analyte is unlabeled and enzyme-labeled analyte is added to the sample to allow the enzyme-labeled analyte in the sample to compete with the unlabeled analyte for binding to the probe;
contacting the support surface with a chemiluminescent substrate which is activated by the enzyme, wherein the activated chemiluminescent substrate excites the energy acceptor dye resulting in emissions therefrom; and
detecting emissions from the energy acceptor dye.

A kit for detecting analyte in a sample is also provided which comprises:
an article of manufacture comprising a support having a surface, an energy acceptor dye on the surface of the support, and one or more biomolecular probes on the surface of the support, wherein the one or more biomolecular probes comprises a probe which is capable of binding to the analyte or, when the analyte is present, which binds to the analyte;
a chemiluminescent substrate; and
optionally, an enzyme-labeled biomolecule or enzyme-labeled analyte. The enzyme-labeled biomolecule can bind to the analyte when the analyte is bound to the surface-bound probe. The enzyme-labeled analyte can compete with unlabeled analyte in the sample for binding to the surface-bound probe.

A method for detecting multiple analytes in a sample is also provided which comprises:
contacting the sample with a first article of manufacture comprising: a support having a surface; a first chemiluminescent enhancing material on the surface of the support; a first energy acceptor dye on the surface of the support; and a first biomolecular probe on the surface of the support, wherein the first biomolecular probe is capable of binding to a first analyte;
contacting the sample with a second article of manufacture comprising: a support having a surface; a second chemiluminescent enhancing material on the surface of the support; an second energy acceptor dye on the surface of the support; and a second biomolecular probe on the surface of the support, wherein the second biomolecular probe is capable of binding to a second analyte;
allowing first analyte in the sample to bind to the first biomolecular probe, wherein: (a) the first analyte is a first enzyme; (b) the first analyte is labeled with a first enzyme; (c) the support surface of the first article of manufacture is contacted with a biomolecule which is labeled with a first enzyme and which binds to the first analyte; or (d) the first analyte is unlabeled and first analyte labeled with a first enzyme is added to the sample to allow the enzyme-labeled first analyte in the sample to compete with the unlabeled first analyte for binding to the first biomolecular probe;
allowing second analyte in the sample to bind to the second biomolecular probe wherein: (a) the second analyte is a second enzyme; (b) the second analyte is labeled with a second enzyme; (c) the support surface of the second article of manufacture is contacted with a biomolecule which is labeled with a second enzyme and which binds to the second analyte; or (d) the second analyte is unlabeled and second analyte labeled with a second enzyme is added to the sample to allow the enzyme-labeled second analyte in the sample to compete with the unlabeled second analyte for binding to the second biomolecular probe;

contacting the first article of manufacture with a first chemiluminescent substrate which is activated by the first enzyme, wherein the activated first chemiluminescent substrate excites the first energy acceptor dye resulting in emissions therefrom and contacting the second article of manufacture with a second chemiluminescent substrate which is activated by the second enzyme, wherein the activated second chemiluminescent substrate excites the second energy acceptor dye resulting in emissions therefrom; and detecting emissions from the first energy acceptor dye and detecting emissions from the second energy acceptor dye, wherein the emissions from the first energy acceptor dye are distinguishable from those of the second energy acceptor dye.

A kit for detecting multiple analytes in a sample is also provided which comprises:

a first article of manufacture comprising: a first support having a surface; a first chemiluminescent enhancing material on the surface of the support; a first energy acceptor dye on the surface of the support; and a first biomolecular probe on the surface of the support, wherein the first biomolecular probe is capable of binding to a first analyte or, when the first analyte is present, which binds to the first analyte;

a second article of manufacture comprising: a support having a surface; a second chemiluminescent enhancing material on the surface of the support; a second energy acceptor dye on the surface of the support; and a second biomolecular probe on the surface of the support, wherein the second biomolecular probe is capable of binding to a second analyte or, when the second analyte is present, which binds to the second analyte;

a first chemiluminescent substrate, wherein the activated first chemiluminescent substrate excites the first energy acceptor dye resulting in emissions therefrom;

a second chemiluminescent substrate, wherein the activated second chemiluminescent substrate excites the second energy acceptor dye resulting in emissions therefrom, wherein the emissions from the first energy acceptor dye are distinguishable from those of the second energy acceptor dye;

optionally, a first enzyme-labeled biomolecule or first analyte labeled with the first enzyme;

optionally, a second enzyme-labeled biomolecule or second analyte labeled with the second enzyme.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

As illustrated in FIG. 6, enzymatic turnover of the dioxetane substrate generates activated chemiluminescent substrate which breaks down to generate light which, through energy transfer (ET), results in fluorescence from the cyanine dye.

DESCRIPTION OF THE VARIOUS EMBODIMENTS

Figure 1:
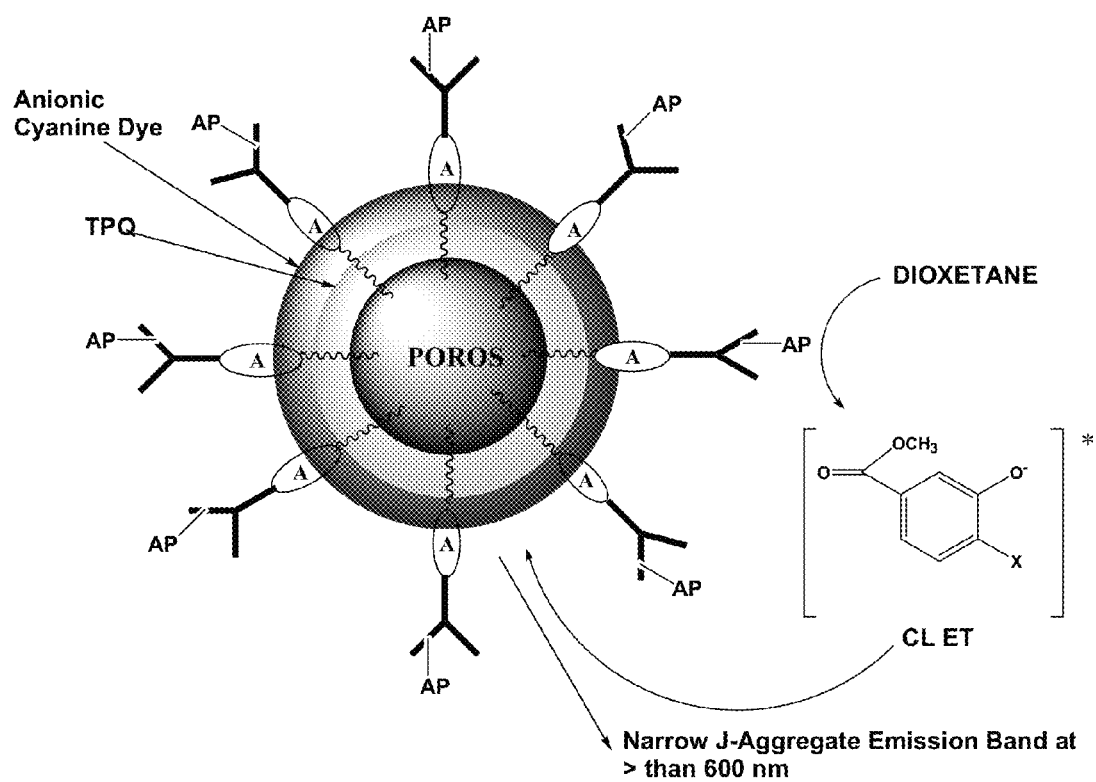
FIG. 1 is a schematic illustrating an assay for alkaline phosphatase labeled IgG antibody wherein a POROS®-A support comprising a chemiluminescent enhancer (i.e., TPQ), an anionic cyanine dye and a biomolecular probe (i.e., protein-A) and having alkaline phosphatase labeled IgG antibody bound to the probe generates chemiexcitation of a chemiluminescent substrate resulting in narrow band emissions from the J-aggregated cyanine dye on the support.

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, an energy acceptor dye is a molecule that is capable of accepting energy via energy transfer (ET) from a donor (e.g., a chemiexcited donor) and transforming the energy to radiation (e.g., luminescence). An exemplary class of acceptor dyes is J-aggregated dyes.

As used herein, a chemiexcited donor is a molecule that can be activated (e.g., by enzyme activation) to populate an excited state fragment from its initial ground energy state. The fragment is capable of transferring its excited state energy to an acceptor molecule as it drops back to a ground state energy level.

As used herein, a molecular filter is a molecule that masks (or quenches) light emissions that interfere with a signal being detected. Non-limiting examples of a molecular filter are hemoglobin, which masks light emission <600 nm and quenching dyes. An example of light emissions that interfere with a signal is autofluorescence (e.g., high energy, blue background emission from biological material).

As used herein, a J-aggregated dye is a dye the molecules of which are associated to form an aggregate which has fluorescent emissions which are red-shifted and narrower in emission bandwidth than that of the monomeric dye species. For example, J-aggregation of certain cyanine dyes can significantly red shift fluorescent emission (i.e., from 530-550 nm for the monomer to 590-620 nm for the J-aggregate) and can narrow the emission bandwidth to approximately 15 nm (fwhm). J-aggregated dyes are disclosed in: T. Kobayashi (ed.), "J-Aggregates", World Scientific Publishing Co., 1996; Whitten et al., "Stabilization of the Aggregation of Cyanine Dyes at the Molecular and Nanoscopic Level," Langmuir, 2000, 16, 9042-9048; Mishra et al., "Cyanines During the 1990s: A Review", Chem. Rev. 2000, 100, 1973-2011; and von Berlepsch et al., "Effect of alcohols on J-aggregation of a carbocyanine dye," Langmuir 2002, 7699-7705.

A general structure of a J-aggregate cyanine dye is set forth below:

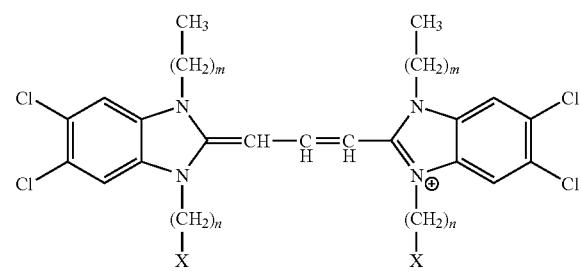

where X=COO$^-$ or SO$_3^-$, m is an integer of 0-9, and n is an integer of 1-9. These dyes have been described in the literature, and are commercially available (e.g., FEW Chemicals, Wolfen, Germany).

As used herein, transfer of energy between donor and acceptor moieties may occur through any energy transfer (ET) process, such as through the collision of the closely associated moieties of an energy transfer set(s) or through a non-radiative process such as resonance energy transfer (RET). It is to be understood that any reference to energy transfer in the instant application encompasses all of these mechanistically-distinct phenomena. It is to be understood that energy transfer can also occur by mechanisms that have not been described or yet thoroughly understood. It is also to be understood that energy transfer can occur through more than one energy transfer process simultaneously and/or sequentially and that detectable signal can be a measure of the activity of two or more energy transfer processes. Accordingly, the mechanism of energy transfer is not a limitation of this invention.

Often, energy transfer will occur by operation of a single donor moiety and a single acceptor moiety, but this is not a limitation. The donor and acceptor moieties can operate such that one or more acceptor moieties accept energy transferred from the one or more donor moieties. It is to be understood that once the energy of chemiexcitation has been transferred to the first acceptor, the energy can then be transferred to a second acceptor and so on through the cascading of energy from subsequent donors to acceptors wherein each energy acceptor is the energy donor in the next energy transfer event.

As used herein, "support" is interchangeable with terms such as "solid support", "solid carrier", "solid phase", "surface", "membrane" or "resin". All 'supports' comprise at least one surface. Surfaces can be planar, substantially planar, or non-planar.

A support can be composed of organic polymers such as polystyrene, polyethylene, polypropylene, polyfluoroethylene, polyethyleneoxy, and polyacrylamide, as well as copolymers and grafts of any of the foregoing. Some other exemplary support materials include, but are not limited to, latex, polystyrene, polytetrafluoroethylene (PTFE), polyvinylidene difluoride (PVDF), nylon, polyacrylamide, or poly(styrene-divinylbenzene) (e.g., POROS®) beads. A support can also be inorganic, such as glass, silica or controlled-pore-glass (CPG). The configuration of a support can be in the form of a bead, a sphere, a particle, a granule, a gel or a membrane. Some non-limiting examples of suitable supports include, but are not limited to, microparticles, nanoparticles, chromatography supports, membranes or microwell surfaces. Supports can be porous or non-porous, and can have swelling or non-swelling characteristics. Supports can be rigid or can be pliable. A support can be configured in the form of a well, depression or other container, vessel, feature or location. A plurality of supports can be configured in an array at various locations, addressable for robotic delivery of reagents, or by detection methods and/or instruments.

The support can have a charged, neutral, hydrophobic or hydrophilic surface. According to some embodiments, a charged support surface can function as a support for a polyelectrolyte multilayer (PEM) coating, produced, for example, by sequential assembly or oppositely charged organic molecules. Polyelectrolyte multilayer coatings are disclosed in Decher et al., eds., "Multilayer Thin Films: Sequential Assembly of Nanocomposite Materials", Wiley-VCH, (2003); Harris et al., "Synthesis of Passivating, Nylon-Like Coatings Through Cross-Linking of Ultrathin Polyelectrolyte Films," J. Am. Chem. Soc., 1999, 121:1978-1979; and in U.S. Patent Application Publication No. 2002-053514 A1. For example, polystyrene beads can be "coated" using hydrophobic adsorption. The support can also be coated using charge interactions, hydrophobic interactions or a combination of these effects. The support itself may be a chemiluminescent enhancer (e.g., nylon). In certain cases, the support surface may be directly derivatized in order to form a construct capable of chemiluminescent enhancement. For example, a support derivatized for chemiluminescent enhancement can be made by partial quaternization of chloromethyl groups on a Merrifield resin (i.e., a polystyrene resin based on a copolymer of styrene and chloromethylstyrene which is cross-linked with divinylbenzene).

As used herein, "support-bound" refers to a compound that is covalently linked to the surface of a support or a compound that is retained in close proximity to a surface of the support. The compound can be retained in close proximity to the surface of the support, for example: 1) by electrostatic interactions with the surface or compounds disposed thereon; 2) by hydrophobic interactions with the surface or compounds disposed thereon; or 3) by a combination thereof. The compound can be retained in close proximity to the surface of the support by entrapment in a polymer layer (e.g. a coating) covering the surface of the support (e.g. U.S. Pat. No. 5,071, 909). By close proximity, it is meant: 1) in some embodiments within about 200 Å of the surface; 2) in some embodiments within about 150 Å of the surface; 3) in some embodiments within about 75 Å of the surface; or 4) in some embodiments within about 50 Å of the surface.

As set forth above, the chemiluminescent enhancing material, energy acceptor dye and the one or more biomolecular probes are, according to some embodiments, "on the surface" of the support. By "on the surface", it is meant that these components are either physically in contact with the surface or else held in close proximity to the surface of the support.

By close proximity, it is meant: 1) in some embodiments within about 200 Å of the surface; 2) in some embodiments within about 150 Å of the surface; 3) in some embodiments within about 75 Å of the surface; or 4) in some embodiments within about 50 Å of the surface. In some embodiments, such as where the surface of the support has been coated with energy acceptor dye and/or a chemiluminescent enhancing material, 'surface' is meant to refer to the interface defined by the coating and bulk solution for the purposes of determining whether a component is held in close proximity to the surface. In some embodiments, 'surface', refers to the surface of the support for the purposes of determining whether a component is held in close proximity to the surface.

In some embodiments the components can be attached either directly or indirectly (e.g., by attachment to an intervening layer covering the surface) to the support surface. The attachment can be chemical (e.g., ionic or covalent attachment) or physical or some combination thereof. For example, the chemiluminescent enhancing material can be coated on the support surface and the resulting construct can be subsequently coated with the energy acceptor dye. Alternatively, the energy acceptor dye can be coated on the support surface and the resulting construct can be subsequently coated with the chemiluminescent enhancing material.

In some embodiments, the components can be retained in close proximity to the surface (this is an example of physical retention). For example, the components can be entrapped in a thin polymer network such that they are available for reaction with other compounds but are not free to escape to bulk solution (See U.S. Pat. No. 5,071,909).

As set forth above, the present invention provides for sensitive homogeneous bioassays on a support, where localized enzyme turnover generates localized chemiexcitation of an acceptor dye, which can be correlated with analyte capture (i.e. determining the presence and/or quantity of the analyte). The resulting enhanced, wavelength-shifted luminescent signal is easily distinguished from non-specific, unenhanced, unshifted signal in bulk solution.

The assays described herein provide a more generalized and simplified assay platform. Incorporation of a support adds a dimension wherein the surface at which the analyte capture occurs has been designed to provide a microenvironment that provides luminescent detection signal distinct from non-specific luminescent signal in bulk solution. The combination of a support having an acceptor dye, a luminescent enhancer, and analyte capture agents enables generation of a luminescent detection signal that can be correlated to analyte capture (for identification and/or quantification) and that is distinguishable from non-specific luminescence. The assay is sensitive because enzyme labels can be used to provide signal amplification. Upon labeled analyte capture at the surface (either in a competitive format with enzyme-labeled analyte, or in a sandwich format with enzyme-labeled detection agent), enzyme activation of a chemiluminescent substrate near the support surface initiates the energy transfer (ET) signal generation that is related to analyte capture. Any loss of enzyme-activated chemiluminescent substrate near the capture event into bulk solution results in non-specific signal distinguishable from ET signal. Because of the differential in quantum yield between the emission that occurs from the enzyme label associated with the capture event on the support containing the assay assembly, and from the unassociated, non-specific enzyme activity in bulk solution, there is no need to separate or wash the excess, non-complexed enzyme-labeled reagent from the support. To further reduce the non-specific light emission, a molecular filter, such as hemoglobin or a quenching dye, can be used in the bulk solution or on the solid support. The wavelength-shifted, enhanced signal can be proportional to the analyte capture event(s). It is possible that with more complex instrument design (e.g., inclusion of wavelength specific filters) complete elimination of the high energy signal from the non-complexed enzyme activity can occur. However, in practice, this should generally not be necessary.

Figure 7:
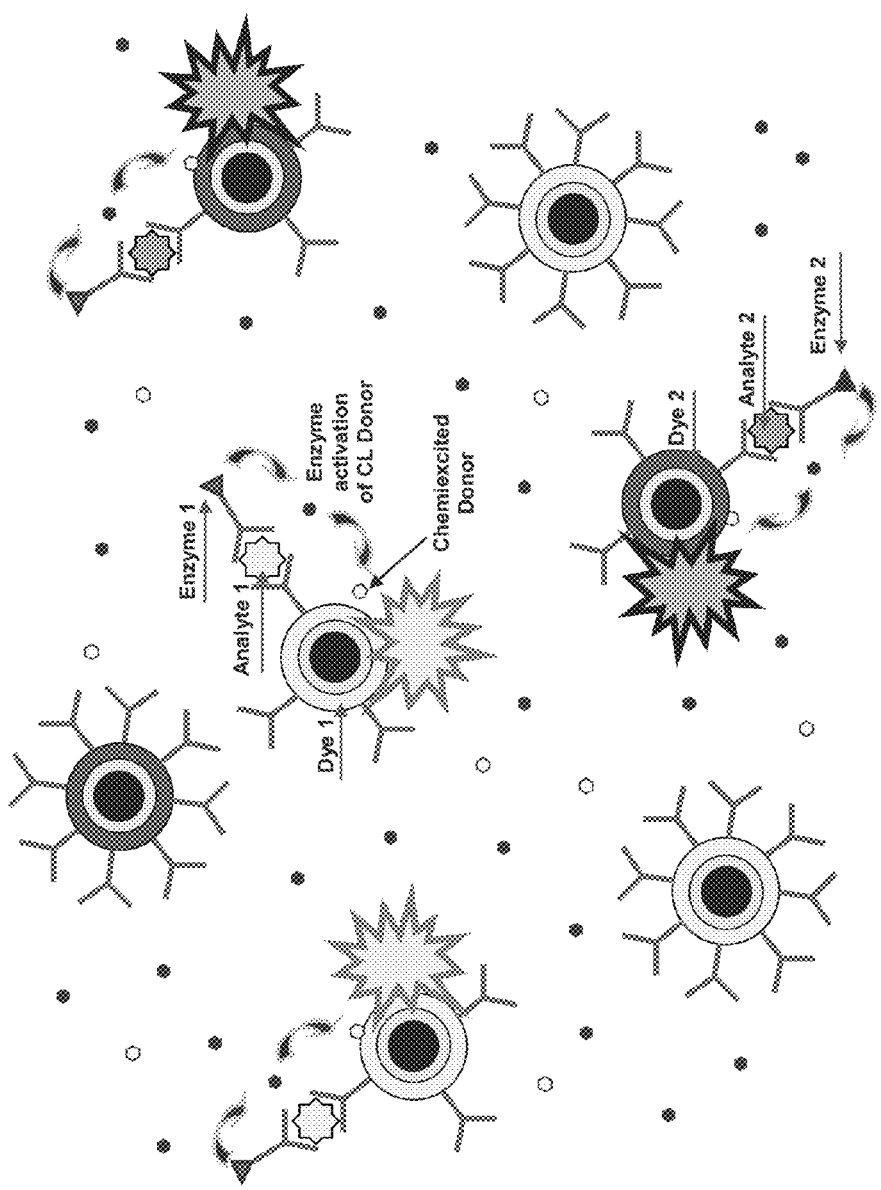
FIG. 7 is a schematic depicting a multiplexed, homogeneous assay.

The combination of an acceptor dye layer, a chemiluminescent enhancer layer, and capture agents on a support, not only facilitates differential signal generation in a homogeneous format, but also enables multiplexed homogeneous assay design. For example, in a homogeneous format, the assay can comprise: 1) a support A, coated with acceptor dye A, a chemiluminescent enhancer, and capture agent A; 2) a support B, coated with an acceptor dye B, a chemiluminescent enhancer, and a capture agent B; and 3) a support C, coated with an acceptor dye C, a chemiluminescent enhancer, and a capture agent C, etc. An multiplexed, homogeneous assay is depicted in FIG. 7. In a multiplexed, homogeneous assay format, each of the chemiluminescent enhancer and/or chemiluminescent substrates can be the same or different, depending on the optimal enzyme-substrate-enhancer combination. The luminescence from acceptor dye A will be distinguishable from acceptor dye B, both of which will be distinguishable from acceptor dye C, and so on. Since it is the signal from the acceptor dye that is measured, it is irrelevant whether or not the same or different chemiluminescent enhancers and/or chemiluminescent substrates are used in the multiplex assay.

In some embodiments, a homogeneous assay that is to be practiced on a support can incorporate an acceptor dye layer of a J-aggregated cyanine dye, a polymeric onium chemiluminescent enhancer, a hydrolytic enzyme label, and a chemiluminescent dioxetane substrate. Capture of enzyme-labeled analyte on the support generates localized chemiexcitation of the J-aggregated dye layer.

This chemiluminescent homogeneous assay has several advantages. For example, chemiexcitation initiated J-aggregated dye luminescence reduces noise, does not require an external excitation light source, and can provide signal significantly red-shifted beyond that generated by any dioxetane decomposition and typical autofluorescence bandwidths associated with biological and cellular materials. The use of J-aggregated dyes as the energy transfer (ET) acceptor provides a significantly red-shifted detection signal. Accordingly, ratiometric data collection is not necessary. In addition, the preferential enhancement of the ET signal on the support at the site of analyte capture compared to the unenhanced, non-specific dioxetane decomposition which may occur in solution further reduces the need for ratiometric measurements. To further reduce the non-specific light emission, a molecular filter, such as hemoglobin or a quenching dye, can be used in the bulk solution or on the solid support. Assay signal detection as a total light measurement on a commercial luminometer circumvents the cumbersome ratiometric measurements on custom dual photo-multiplier tube (PMT) luminometers described in earlier ET-based bioassays {See, e.g., Patel et al., "Chemiluminescence Energy Transfer: A New Technique Applicable to the Study of Ligand-Ligand Interactions in Living Systems", Analyt. Biochem. 129:162-169 (1983); Patel et al., "Homogeneous Immunoassay Based On Chemiluminescence Energy Transfer", Clin. Chem. 29/9, 1604-1608 (1983); Williams et al., "A Homogeneous Assay For Biotin Based On Chemiluminescence Energy Transfer", Analyt. Biochem., 155:249-255 (1986)}. Enzyme labeling instead of direct chemiluminescent substrate labeling can also be used to amplify the detection signal to increase detection sensitivity limits. The assays described herein, for example, can demonstrate a dynamic range of 3 orders of magnitude, and assay optimization can further increase analyte detection sensitivities in a general ET homogeneous assay design (See FIG. 4 and Example B).

The assay system described herein enables detection of an analyte present (e.g. captured) on a support surface by energy transfer (ET) from activated chemiluminescent substrates (i.e., chemically excited state donors) to dye acceptors (e.g., fluorescent acceptor dyes and/or J-aggregated dyes). The wavelength-shifted emission characteristics of dye acceptors allow the design of bioassay systems that provide discrete detection signals red-shifted from typical biomolecular or cellular background fluorescence. A specific example is the use of J-aggregated dyes that provide sharp, narrowed, discrete detection signals significantly red-shifted from autofluorescence.

The general assay design can accommodate any chemiluminescent enzyme substrate (e.g., dioxetanes, acridinium esters, acridinium sulfonimides, acridans, acridanenolphosphates, luciferin and luminols) and chemiluminescent surface signal enhancers that tailor the charge environment of the support surface for optimal analyte signal generation and discrimination. For example, the assay system can comprise a support coated with a chemiluminescent enhancing polymer and a dye, wherein the support comprises one or more surface-bound biomolecular probes suitable for capture of an analyte. When the analyte is captured, this event can be detected by a chemiluminescent signal, for example from chemiexcited dioxetane fragments, generated by an enzyme label or enzyme analyte. The chemiluminescent signal generated by captured analyte is easily distinguishable from non-specific signal such that the desired signal is wavelength-shifted and enhanced and emanates from the acceptor dye 'on the surface' of the support. This compares with the non-specific signal that is not wavelength-shifted and is unenhanced and that emanates from bulk solution. The assay can be used to identify and/or quantify the captured analyte.

The bioassay system can use chemiexcitation at wavelengths of approximately 460 nm to 590 nm in an energy transfer mode to generate red-shifted acceptor dye emission. An example of chemiexcitation at a wavelength of approximately 460 nm to generate J-aggregate dye emission at a wavelength of approximately 610 nm generates a Stokes shift of approximately 150 nm. This large Stokes shift enables simplification of signal detection and quantification, where signal quantification can be done as a total light measurement on commercially available luminometers, with no need for dual filter readings or dual photo-multiplier tube (PMT) readings on custom luminometers, and no need for conversion to ratiometric data. Simplified data collection as a total light read is further facilitated by preferentially enhancing the signal corresponding to surface-bound (i.e. captured) analyte.

The chemiluminescent enhancing material can be a water-compatible synthetic or naturally-occurring material that can provide a hydrophobic micro-environment of reduced protonicity for the light-emitting fragments resulting from the enzymatic activation of the chemiluminescent substrate in a polar medium (i.e., a medium consisting of water as a solvent or a mixture of water and other largely or entirely polar substances, such as methanol, acetonitrile, dimethylsulfoxide, dimethylformamide and the like). Depending on the precise nature of the micro-environment, the chemiluminescent signal, and/or the chemiluminescent signal to noise ratio can be higher in the presence of the chemiluminescent enhancing material since the chemiluminescent enhancing material can prevent environmental quenching of the chemiluminescent emission from the light-emitting fragments. Additionally, the signal can be more spatially resolved than in the substantially aqueous environment alone since the presence of the chemiluminescent enhancing material can minimize diffusion of the light-emitting fragment resulting from the enzymatic activation of the chemiluminescent substrate from the site at which the enzyme reaction occurs.

The chemiluminescent enhancing material can be a macromolecular globular protein having hydrophobic regions. The globular proteins can have molecular weights ranging from about 1,000 to about 800,000 daltons, and preferably from 40,000 to about 100,000 daltons, as determined by sodium dodecyl sulfate (SDS) gel electrophoresis. Exemplary globular proteins include, but are not limited to mammalian serum albumins such as bovine serum albumin (BSA) and human serum albumin (HAS) and mammalian Immunoglobulin G (IgG), Immunoglobulin E (IgE), Protein A, and avidins.

The chemiluminescent enhancing material can be a synthetic macromolecular substance (e.g., an oligomeric or polymeric chemiluminescent enhancing material). Exemplary synthetic macromolecular chemiluminescent enhancing materials include water-soluble or water-compatible, solvent soluble polymeric onium salts. A wide variety of polymers of this class have been utilized in the prior art as mordents, or image-receiving layers, in diffusion transfer photographic systems. The onium functionality may be located in the backbone of the polymer (ionenes) or on a group pendant to the backbone. The positively charged, onium functional groups are normally based on nitrogen, phosphorus, or sulfur; however any positively charged grouping may be used. Any of these polymers may be used as macromolecular chemiluminescence enhancing materials. Exemplary of this large class of materials are poly(vinylbenzyl quaternary ammonium salts) having the formula:

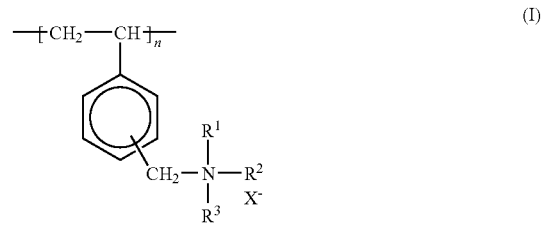

(I)

In this formula each group, $R^1$, $R^2$ and $R^3$, each independently represent:

a straight or branched chain unsubstituted alkyl or alkenyl group having from 1 to 20 carbon atoms inclusive (e.g., methyl, ethyl, n-butyl, t-butyl, cetyl, or the like);

a straight or branched chain alkyl group having from 1 to 20 carbon atoms, inclusive, substituted with one or more hydroxy, alkoxy (e.g., methoxy, ethoxy, benzyloxy, or polyethyleneoxy), aryloxy (e.g., phenoxy), amino or substituted amino (e.g., acetamido or cholesteryloxycarbonylamido), or halogen or fluoroalkane or fluoroaryl (e.g., heptafluorobutyl) groups;

an unsubstituted monocycloalkyl group having from 3 to 12 ring carbon atoms inclusive (e.g., cyclohexyl or cyclooctyl);

a substituted monocycloalkyl group having from 3 to 12 ring carbon atoms, inclusive, substituted with one or more alkyl, alkoxy, haloakyl, or fused benzo groups (e.g., dimethylcyclohexyl or tetrahydronaphthyl);

a polycycloalkyl having two or more fused rings, each having from 5 to 12 carbon atoms, inclusive, unsubstituted or substituted with one or more alkyl, alkoxy or aryl groups (e.g., 1-adamantyl or 3-phenyl-1-adamantyl);

an aryl, alkaryl, or aralkyl group having at least one ring and from 6 to 20 carbon atoms in total, unsubstituted or substituted with one or more alkyl, aryl, halogen, fluoroalkyl or fluoroaryl groups (e.g., phenyl, naphthyl, pentafluorophenyl, ethylphenyl, benzyl, chloro- or fluorobenzyl or phenylbenzyl);

At least two of the above R groups (i.e., $R^1$, $R^2$ or $R^3$ groups), together with the quaternary atom to which they are bonded, can form a saturated or unsaturated, unsubstituted or substituted nitrogen-containing, nitrogen and oxygen-containing, or nitrogen and sulfur-containing ring having from 3 to 5 carbon atoms, inclusive, and 1 to 3 heteroatoms, inclusive, and which may be benzoannulated, e.g., 1-pyridinium, 1-(3-alkyl or aralkyl)imidazolium, morpholinium, alkyl or acylpiperidinium, benzoxazolium, benzothiazolium, or benzimidazolium groups.

The symbol $X^-$ represents an anionic counterion, which can include alone, or in combination, moieties such as halide (e.g., chloride or bromide), sulfate, alkylsulfonate (e.g., methanesulfonate), triflate, arylsulfonate (e.g., p-toluenesulfonate), perchlorate, alkanoate (e.g., acetate), arylcarboxylate, or a fluorescent counterion (e.g., fluorescein or fluorescein derivatives), 9,10-diphenylanthracene sulfonate, or sulforhodamine derivatives.

The symbol n can represent a number such that the molecular weight of the poly (vinylbenzyl) quaternary ammonium salts will range from about 8,000 to 1,000,000 or more as determined by a low angle laser light scattering (LALLS) technique.

Other exemplary polymeric onium salts which can be used as chemiluminescent enhancing materials include the phosphonium or sulfonium polymers depicted in the following formulae, wherein the definitions for groups, R, $X^-$ and n are as given above.

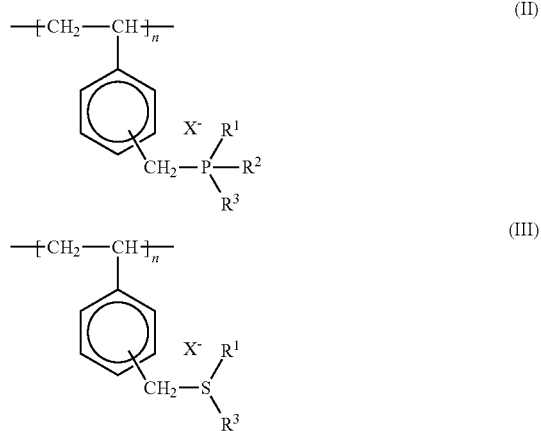

Furthermore, copolymers containing two or more different pendant onium groups may also be used as chemiluminescent enhancing materials. These may be random or block copolymers, which can be synthesized using methods recognized in the art. These copolymers can include the combination of recurring units shown below in formula IV or formula V:

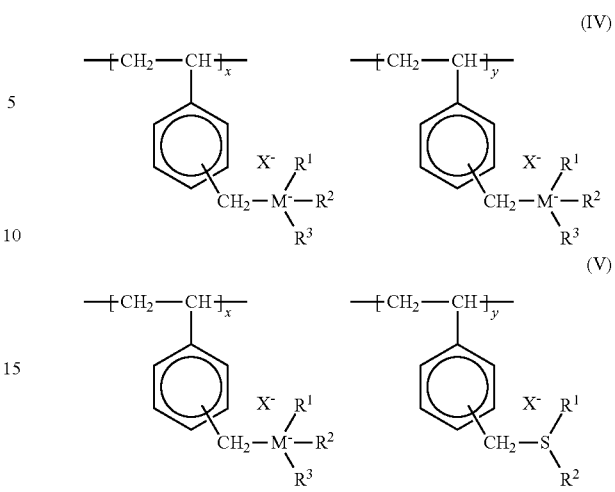

In the above formulae, M may be nitrogen, or phosphorus. Each of the $R^1$, $R^2$ and $R^3$ groups and each $X^-$ are as defined above. In formula IV, one or more of the M, $R^1$, $R^2$ or $R^3$ substituents in one of the pendant onium moieties are different than the corresponding substituent in the other pendant onium moiety. The symbols, x and y, represent the mole fraction of the individual monomers comprising the copolymer. The symbols, x and y, may thus individually vary from 0.01 to 0.99, with the sum of x and y equaling one.

Copolymers or block copolymers wherein one of the monomers is an ethylenically unsaturated onium monomer and the other (or others) is charge-neutral can also be used as chemiluminescent enhancing materials. These and other macromolecules capable of providing enhancement of the light emission from chemiluminescent species, such as enzyme-activated 1,2-dioxetanes, can be found in U.S. Pat. Nos. 5,145,772 and 5,827,650. Both of these patents are incorporated herein by reference in their entirety.

Dicationic surfactants can also be using as chemiluminescent enhancing materials. These dicationic surfactants can be represented by the following formula:

$$X^-(R^4)_3A^+CH_2\text{-[LINK]-}CH_2A^+(R^5)_3X^-$$

wherein:
each A is independently selected from the group consisting of phosphorus and nitrogen atoms;
$X^-$ is an anionic counterion;
each $R^4$ and $R^5$ is independently selected from the group consisting of unsubstituted and substituted alkyl and aralkyl groups containing 1 to 20 carbon atoms such that $R^4$ and $R^5$ can be the same or different; and
[LINK] is a carbon chain selected from the group consisting of dialkylenearyl, aryl, alkylene, alkenylene and alkynylene groups containing 4 to 20 carbon atoms. Dicationic surfactants which can be used as chemiluminescent enhancers are described in U.S. Pat. No. 5,451,347, which is herein incorporated by reference in its entirety.

Other water soluble oligomeric, homopolymeric and copolymeric materials can be used as enhancer substances in addition to or instead of the foregoing polymers, including:
poly-N-vinyl oxazolidinones;
polyvinyl carbamates (e.g., polyvinyl propylene carbamate);
polyhydroxyacrylates and methacrylates [e.g., poly(β-hydroxyethyl)methacrylate and polyethyleneglycol monomethacrylates];

amine-containing oligomers (e.g., Jeffamines) quaternized with alkylating or aralkylating agents;

synthetic polypeptides (e.g., polylysine or phenylalanine); polyvinylalkylethers (e.g., polyvinyl methyl ether);

polyacids and salts thereof [e.g., polyacrylic acids, polymethacrylic acids, polyvinylbenzoic acid, polyethylenesulfonic acid, polyacrylamidomethylpropanesulfonic acid, polymaleic acid and poly(N-vinyl succinamidic acid)];

polyacrylamides and polymethacrylamides derived from ammonia or cyclic and acyclic primary or secondary amines;

polyvinyl alcohol and polyvinyl alcohol copolymers with vinyl acetate, ethylene and the like;

poly 2-, 3- or 4-vinylpyridinium salts where the heterocyclic nitrogen atom is bonded to a group as defined for $R^1$, $R^2$ and $R^3$ in formula I above;

polyvinylalkylpyrrolidinones (e.g., polyvinylmethylpyrrolidinones);

polyvinylalkyloxazolidones (e.g., polyvinylmethyloxazolidones);

branched polyethyleneimines, acylated branched polyethyleneimines, or acylated branched polyethyleneimines further quaternized with alkyl or aralkyl groups;

poly N-vinylamines derived from ammonia or cyclic and acyclic primary or secondary amines, and quaternary salts thereof;

polyvinylpiperidine; or polyacryloyl, polymethacryloyl or 4-vinylbenzoyl aminimides or polyvinylbenzyl aminimides where the other substituents on the positively charged nitrogen atom may be any of the $R^1$, $R^2$ and $R^3$ groups defined in formula I above.

The above described oligomeric or polymeric chemiluminescent enhancing materials can have molecular weights within the ranges given above for the poly(vinylbenzyl quaternary ammonium salts) of formula I.

Positively charged water-soluble or water-compatible, solvent soluble small molecule onium salts can also be used as chemiluminescent enhancing materials to enhance chemiluminescent signals on supports. The small molecule onium salts can have positively charged onium groups on nitrogen, phosphorus or sulfur, or include any other positively charged grouping in the structure. The counterion can include, either alone or in combination, moieties such as halide (e.g., chloride or bromide), sulfate, alkylsulfonate (e.g., methanesulfonate), triflate, arylsulfonate (e.g., p-toluenesulfonate), perchlorate, alkanoate (e.g., acetate), arylcarboxylate, or a fluorescent counterion.

The chemiluminescent enhancing effect of the polymers described above can be modulated by use of chemiluminescent enhancement additives as described in U.S. Pat. No. 5,547,836. The chemiluminescent enhancement additive can be applied to the support surface prior to or after application of the chemiluminescent enhancing material to the surface. Alternatively, the chemiluminescent enhancement additive can be mixed with the chemiluminescent enhancing material and the resulting mixture applied to the support surface.

The chemiluminescent enhancement additive can improve the ability of the chemiluminescent enhancing material to form hydrophobic regions in which the dioxetane oxyanion and the resulting emitter can be sequestered, permitting decomposition and chemiluminescence in the absence of water, and therefore, reducing light-quenching reactions caused thereby. The enhancement additives can be drawn from any of a wide variety of compounds. Exemplary enhancement additives include surfactants (e.g., detergents), negatively charged salts and solvents. Surfactants can improve the ability of the chemiluminescent enhancing material to form a hydrophobic region which is relatively stable.

The surfactants may be cationic, anionic, zwitterionic or neutral. Another class of enhancement additives which, when added to the solution, appear to improve the ability of the enhancement material to sequester the active dioxetane species, and in any event, lead to further enhancement of the chemiluminescent signal, include negatively charged salts. A third class of enhancement additives also active at very low concentrations are hydrophobic solvents including, but not limited to, alcohols.

A fourth effective class of enhancement additives is non-quaternary water-soluble polymers, such as poly(2-ethyl-Z-oxazoline) (PolyOx). While these polymers themselves may induce limited enhancement of the chemiluminescent signal without an increase in background noise, the use of non-quaternary water-soluble polymers in conjunction with polymeric quaternary onium salt enhancement materials can improve the chemiluminescent signal on supports such as microarrays.

Further improvements in chemiluminescent signal and signal to noise (S/N) can be obtained by independently combining one or more enhancement materials (e.g., globular proteins, synthetic onium or non-onium polymers or copolymers) and one or more enhancement additives.

The chemiluminescent enhancing polymer can be a TPQ polymer which has a structure as set forth below.

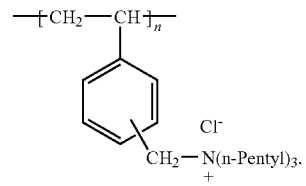

Other exemplary chemiluminescent enhancing polymers include, but are not limited to, poly(vinylbenzyldimethylbenzylammonium chloride) (BDMQ), poly(vinylbenzyltrimethylammonium chloride) (TMQ), poly(vinylbenzyltributylammonium chloride) (TBQ), poly(vinylbenzyltributylphosphonium chloride) (TB), poly(vinylbenzyltrioctylphosphonium chloride) (TO) and copolymers thereof.

The acceptor dye can be chosen from any fluorescent compound which has a lower energy for its singlet excited states compared to the excited state of the chemiluminescent substrate. Resonance energy transfer from the chemiluminescent substrate to the acceptor dye results in red-shifted emission. Examples of acceptor dyes include, but are not limited to: fluorescent dyes; aromatic compounds including naphthalenes, anthracenes, pyrenes, biphenyls; acridine; coumarins; xanthenes; phthalocyanines, stilbenes; furans, oxazoles, oxadiazoles; and benzothiazoles. Exemplary dyes which can be used as energy acceptor dyes are also disclosed in U.S. Pat. Nos. 6,028,190; 6,335,440 B1; 6,849,745 B2; and 7,169,939 B2.

The dye can be chosen from dyes that are capable of forming J-aggregates on the support surface (e.g., cyanines). The ability of the dye to form J-aggregates on the support surface allows for homogeneous chemiluminescent assay design. J-aggregated dyes exhibit a very characteristic narrow bandwidth (e.g., 15-20 nm fwhm), and emission significantly red-shifted (e.g., approximately 80-250 nm) from monomeric dye emission (e.g., approximately 530 nm), dioxetane emission (e.g., approximately 460 nm to 590 nm), and biomolecular or cellular background luminescence (e.g., approximately 350 nm).

The cyanine dye can be an anionic cyanine dye. The anionic cyanine dye can have a structure as set forth below:

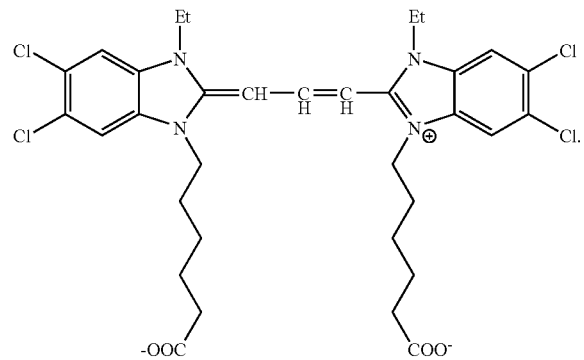

The support can have a negatively charged surface which is coated with a cationic chemiluminescent enhancing material (e.g., a cationic homopolymer or copolymer having positively charged onium groups). If the support has a negatively charged surface, the negatively charged surface can be coated with a cationic chemiluminescent enhancing material. The resulting construct can then be coated with an anionic acceptor dye. Alternatively, if the support has a positively charged surface, the surface can be coated with an anionic acceptor dye, followed by a cationic chemiluminescent enhancing material. The sequence of coating dye and enhancer layers on the support, and the physical characteristics of the dye and enhancer (i.e., the charge and/or the hydrophobicity), can be varied to obtain effective multilayer coating of dye and enhancer on the support surface.

In some embodiments, the acceptor dye and the chemiluminescent enhancer can be commingled in a single layer or integrated with the support. Exemplary formulations including chemiluminescent enhancers and dyes are disclosed in U.S. Pat. No. 5,145,772. In some embodiments, the acceptor dye and/or chemiluminescent enhancer can be entrapped in a polymer network. When the chemiluminescent enhancer is a polymer, the enhancer can be formulated to form a thin coating on the surface and entrap the acceptor dye or a modified version of the acceptor dye. For example, an acceptor dye labeled peptide can be entrapped in a layer comprising a polymeric chemiluminescent enhancer. Methods of entrapping peptides are disclosed in U.S. Pat. No. 5,071,909. For example, a dye can be linked to the polypeptide and the resulting construct can be entrapped using the methods disclosed in U.S. Pat. No. 5,071,909.

The molecular filter can be any molecule that masks or quenches light emissions that interfere with a signal being detected. Examples of molecular filters include, but are not limited to, hemoglobin and quenching dyes, such as dabcyl, DPX (Invitrogen #X1525) and DNP C2 amine (Anaspec #81821). Any molecule which masks or quenches light emissions that interfere with a signal being detected can be used.

The biomolecular probes can be or can comprise antibodies, polynucleotides, oligonucleotides, polypeptides, proteins, receptors, lectins and/or aptamers. In some embodiments, the biomolecular probe comprises a probe wherein the probe is an antibody, a polynucleotide, an oligonucleotide, a polypeptide, a protein, a receptor, a lectin and/or an aptamer.

The enzyme analyte or enzyme label can be any enzyme capable of activating a chemiluminescent substrate. Examples are oxidative enzymes, such as horseradish peroxidase, and hydrolytic enzymes, including but not limited to, alkaline phosphatase, beta-galactosidase, glucuronidase and neuraminidase. In the case of an immunoassay, upon capture of the analyte, the capture event can be detected with a hydrolytic enzyme label, attached to a detector antibody in a sandwich assay format or attached to the captured analyte.

When using a dioxetane as the chemiluminescent substrate, fragmentation can be initiated by hydrolytic enzyme activation. By this event, the potential energy of the chemiluminescent substrate (e.g., the potential energy of the four-membered peroxide ring of a dioxetane substrate) is released to excite the aryl ester fragment to a singlet excited state. Relaxation of the singlet excited state fragment to ground state transfers energy to a proximal acceptor dye (e.g., a J-aggregated dye) on the support surface, which can then luminesce. If the energy acceptor is a J-aggregate, the emission is narrow and red-shifted.

As set forth above, the chemiluminescent substrate can be a 1,2-dioxetane substrate. For example, the 1,2-dioxetane chemiluminescent substrate can be CDP-Star®, available from Applied Biosystems. CDP-Star® has the chemical name disodium 2-chloro-5-(4-methoxyspiro {1,2-dioxetane-3,2'-(5'-chloro)-tricyclo[3.3.1.1$^{3,7}$]decan}-4-yl)-1-phenyl phosphate and a chemical structure as set forth below:

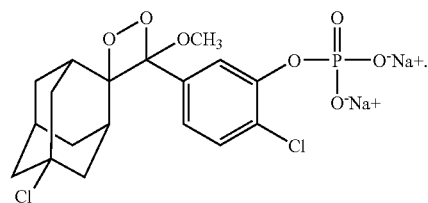

The 1,2-dioxetane chemiluminescent substrate can be CSPD®, which is also available from Applied Biosystems. CSPD® has the chemical name disodium 3-(4-methoxyspiro {1,2-dioxetane-3,2'-(5'-chloro)tricyclo[3.3.1.1$^{3,7}$]decan}-4-yl)-1-phenyl phosphate and a chemical structure as set forth below:

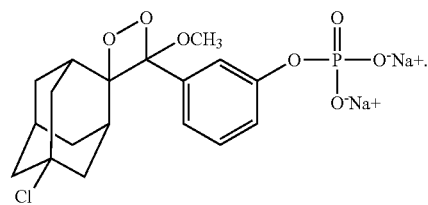

The 1,2-dioxetane chemiluminescent substrate can be TFE-CDP-Star® which is also available from Applied Biosystems and which has a chemical structure as set forth below:

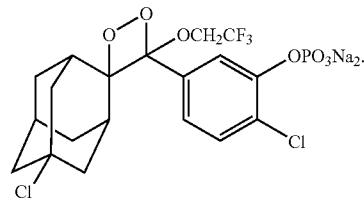

The aforementioned 1,2-dioxetane chemiluminescent substrates are merely exemplary and other 1,2-dioxetane substrates can be used.

The analyte in an assay can be any analyte of interest for which there exists a compound (i.e. a probe or biomolecular probe) to which the analyte is known to specifically bind. For example, the analyte can be an enzyme. Alternatively, the analyte can be a compound labeled with an enzyme, or an enzyme-labeled biomolecule which binds the analyte when the analyte is bound to a probe on the support. In some embodiments, the analyte can be unlabeled and can compete for binding to the biomolecular probes on the support surface with enzyme-labeled analyte which has been added to the sample.

The enzyme label can be alkaline phosphatase. The chemiluminescent substrate can be CSPD® or CDP-Star® and the enzyme label can be alkaline phosphatase.

A method for detecting multiple analytes in a sample is also provided. The method comprises contacting the sample with a first article of manufacture comprising: a support having a surface; a first chemiluminescent enhancing material on the surface of the support; a first energy acceptor dye on the surface of the support; and a support-bound first biomolecular probe comprising a first probe capable of binding to a first analyte. According to the method, the first probe binds to a first analyte when present in the sample.

The method also comprises contacting the sample with a second article of manufacture comprising: a support having a surface; a second chemiluminescent enhancing material on the surface of the support; an second energy acceptor dye on the surface of the support; and a support-bound second biomolecular probe comprising a second probe capable of binding to a second analyte. According to the method, the second probe binds to a second analyte when present in the sample.

First and second analyte in the sample are then allowed to bind to the first and second probe, respectively.

For an assay which utilizes enzyme amplification, one of the following conditions may apply: (a) the first analyte is a first enzyme; (b) the first analyte is labeled with a first enzyme; (c) the support surface of the first article of manufacture is contacted with a biomolecule which is labeled with a first enzyme (and which is capable of binding to the first analyte when the first analyte is bound to the first probe on the support surface); or (d) the first analyte is unlabeled and first analyte labeled with a first enzyme is added to the sample to allow the enzyme-labeled first analyte in the sample to compete with the unlabeled first analyte for binding to the first probe of the first article of manufacture. Corresponding conditions may apply with respect to the second analyte, second enzyme, second probe and second article of manufacture.

After the first and second analyte in the sample are allowed to bind to the first and second probes, respectively, the first article of manufacture is contacted with a first chemiluminescent substrate which is activated by the first enzyme. The activated first chemiluminescent substrate excites the first energy acceptor dye resulting in emissions therefrom. Similarly, the second article of manufacture is contacted with a second chemiluminescent substrate which is activated by the second enzyme. The activated second chemiluminescent substrate excites the second energy acceptor dye resulting in emissions therefrom.

Emissions from the first energy acceptor dye and emissions from the second energy acceptor dye are then detected. The emissions from the first energy acceptor dye can be distinguished from those of the second energy acceptor dye.

In the multiplexed assay, the first and second chemiluminescent substrates can be the same or different. The first and second chemiluminescent enhancing materials can also be the same or different. In addition, the first and second articles of manufacture can be contacted with the sample simultaneously or sequentially. The first and second articles of manufacture can also be contacted with the first and second chemiluminescent substrates simultaneously or sequentially. Emissions from the first energy acceptor dye and emissions from the second energy acceptor dye can also be detected simultaneously or sequentially.

While enzyme amplification has been described above, chemiluminescent labels can also be used. In particular, the analyte can be labeled with a chemiluminescent label. Alternatively, the support surface can be contacted with a biomolecule which is labeled with a chemiluminescent label and which binds to the analyte when the analyte is bound to the probe on the support. As a further alternative, the analyte can be unlabeled and analyte labeled with a chemiluminescent label can be added to the sample prior to allowing the analyte in the sample to bind to the probe thereby competing with the unlabeled analyte for binding to the probe. The chemiluminescent label can then be activated. Energy transfer from the activated chemiluminescent label to the energy acceptor dye on the support results in luminescence which can be detected and which can be used to determine the presence and/or the amount of analyte in the sample.

EXAMPLES

Aspects of the present teachings may be further understood in light of the following examples, which should not be construed as limiting the scope of the present teachings in any way.

A. IgG-AP Assay

POROS®-A was used as the support for a model bioassay study for several reasons. Protein A-coated POROS® exhibits an overall weak negative surface charge, which allows for coating with a cationic polymeric chemiluminescent enhancer, such as TPQ, followed by coating with an anionic cyanine dye (e.g., to form a POROS®/TPQ/cyanine dye construct, such as the one illustrated in FIG. 1). Based on the ease of inducing J-aggregation on POROS®-HS, which also has an overall negative charge, an anionic cyanine dye coated on POROS®-A was expected to also form J-aggregates on the support surface.

Protein A and IgG antibody association can be done in one step by simply incubating Protein A and IgG together to form a very tight complex ($K_a=10^9$ M) (Akerstrom et al., "A Physicochemical Study of Protein G, a Molecule with Unique Immunoglobulin G-Binding Properties," J. Biol. Chem., 1986, 261:10240-10247). If IgG antibody labeled with alkaline phosphatase is introduced into a solution containing the POROS®-A/TPQ/J-aggregate construct, the analyte (alkaline phosphatase) will be captured on the POROS® surface coated with J-aggregated cyanine and TPQ enhancer. The analyte detection is then based on the proximity of signal generation (e.g., chemiexcitation of the J-aggregate dye coating by an excited state dioxetane fragment) occurring near or on the J-aggregated dye surface. To obtain efficient energy transfer to the J-aggregate cyanine coating, the chemiexcited dioxetane fragment can be within a 0 to 100 angstrom (i.e., 0-10 nm) distance from the J-aggregate assembly (Lakowicz, "Principles of Fluorescence Spectroscopy", 2nd ed., Kluwer Academic/Plenum Press, p. 388).

As shown in FIG. 1, the blue 460 nm energy state of dioxetane CDP-Star®, generated by surface-captured alkaline phosphatase undergoes surface TPQ enhancement and energy transfer to produce J-aggregate emission at approximately 600 nm with a narrow emission bandwidth. Although some blue chemiluminescent signal centered at 460 nm may be observed, this should be minimal due to a lack of polymeric enhancement in the aqueous phase. For a homogeneous assay, only the red fluorescent signal (590-620 nm) may be measured for analyte detection and quantification. The signal can be correlated to events happening at the POROS®-A surface.

A POROS®-A/TPQ/J-aggregate construct was used in a homogeneous assay of alkaline phosphatase as the analyte. Upon introducing IgG antibody labeled with alkaline phosphatase into a solution containing the POROS®-A/TPQ/J-aggregate construct, the analyte (alkaline phosphatase) was captured by Protein A on the POROS® surface coated with J-aggregated cyanine and TPQ enhancer. The analyte was detected based on the proximity of signal generation (e.g., chemiexcitation of the J-aggregate coating by an excited state dioxetane fragment) occurring near or on the J-aggregate coated surface. The blue 460 nm dioxetane CDP-Star® excitation, generated by surface-captured alkaline phosphatase, underwent surface TPQ enhancement and energy transfer to produce J-aggregate emission at approximately 600 nm with a narrow emission bandwidth. Any blue chemiluminescent signal (460 nm max), arising from inefficient energy transfer, was minimized due to the lack of polymeric enhancement in the aqueous phase. For a homogeneous assay, only the red fluorescent signal (590-620 nm) can be measured for analyte detection and quantification. This signal, which is produced by the J-aggregated dye on the POROS®-A surface, correlates to events happening at the POROS®-A surface.

The energy transfer efficiency from CDP-Star® to cyanine J-aggregates captured on the POROS®-20A surface was measured as the ratio of red/blue signal intensities from a 96-microtiter plate on the Carey Eclipse fluorimeter. Each well contained a mixture of 10 µl of a series of 1:2 dilutions of POROS®-20A/IgG-AP/TPQ dye constructs in BSA/PBS and 90 µl of 0.4 mM CDP-Star® in AMP buffer at pH 9.5. The spectra and data are summarized in the table below.

| Intensity Ratios from POROS ® 20A/IgG-AP/TPQ/dye Dilutions and CDP-Star ® | | | | |
|---|---|---|---|---|
| | | POROS ®-20A/IgG-AP/TPQ Dye Construct Dilutions | | |
| | | ½ | 1/32 | 1/64 |
| Carey Detector (PMT) | | 700 | 1000 | 1000 |
| CDP-Star ® | $\lambda_{max}$ (nm) | 442 | 443 | 447 |
| | Intensity (a.u.) | 8.5 | 62 | 55 |
| J-aggregate | $\lambda_{max}$ (nm) | 615 | 597 | 598 |
| | Intensity (a.u.) | 393 | 878 | 662 |
| Ratio of J-Agg/CDP-Star ® Int. (red/blue) | | 46 | 14 | 12 |

Energy transfer efficiencies were excellent as shown by the presence of predominant J-aggregate emission signal at 597-615 nm. The residual dioxetane emissions at 442-447 nm were only detected in lower dilution experiments, but the intensity ratios were still high (Red:Blue Intensity ratio=12 even at 1/64 dilution of acceptor).

A series of experiments were also performed to determine relative detection curves for analyte capture (IgG-AlkPhos) on the POROS®-20A construct surface. The detection limit for alkaline phosphatase was determined by incubating a series of rabbit anti-mouse IgG-AP dilutions in AMP buffer with standard mixtures of POROS® 20A/TPQ/anionic cyanine dye assembly in BSA/PBS and 0.4 mM CDP-Star® in AMP-Cl buffer at pH 9.5. The detection curves were generated from the total chemiluminescent signals on the Turner Luminometer, with and without a 600 nm broadband filter.

Protocol of IgG-AP Detection Assay
POROS® Construct Preparation
1. Pipette 0.15 ml (25 mg) of POROS®-20A slurry and suspend in 0.85 ml of $H_2O$.
2. Centrifuge and discard supernatant.
3. Wash beads in 1 ml of $H_2O$ 3 times.
4. Suspend beads in 1 ml of TPQ stock solution (2 mg/ml $H_2O$).
5. Incubate 60 minutes on a plate shaker.
6. Discard supernatant and wash beads sequentially in 1 ml of water twice and 1 ml of 40% MeOH/$H_2O$ once.
7. Suspend beads in 40% MeOH/$H_2O$ and add 20 µl of dye stock solution (100 mg/2 ml MeOH).
8. Wrap in aluminum foil and incubate 60 minutes on a plate shaker.
9. Discard orange supernatant which forms pink emulsion in aqueous solution.
10. Wash pink color beads sequentially in 1 ml of $H_2O$ and 1 ml of BSA/PBS 3 times.
11. Suspend the final beads in 1 ml of BSA/PBS and store in dark in refrigerator.

IgG-AP Conjugate Assay
1. Prepare a series of 1:10 IgG-AP dilutions.
2. Place 10 µl of POROS® construct in a test tube.
3. Add 10 µl of IgG-AP dilution to test tube.
4. Incubate the mixture at room temperature for 10 minutes.
5. Add 80 µl of 0.4 mM CDP-Star®.
6. Gently shake the mixture at room temperature for 30 or 60 minutes.
7. Place test tube in Turner luminometer at 37° C. and collect signal immediately for 10 minutes.

Detection Limit: 1:100 million dilution of IgG-AP gives S/N>2 (60 minute 0.4 mM CDP-Star® incubation; no filters for readout)

The detection limit (S/N>2) improved 10-fold from 1:10 million to 1:100 million dilution of IgG-AP upon doubling CDP-Star® incubation time to 60 minutes.

B. Competitive cAMP Assay

Figure 2:
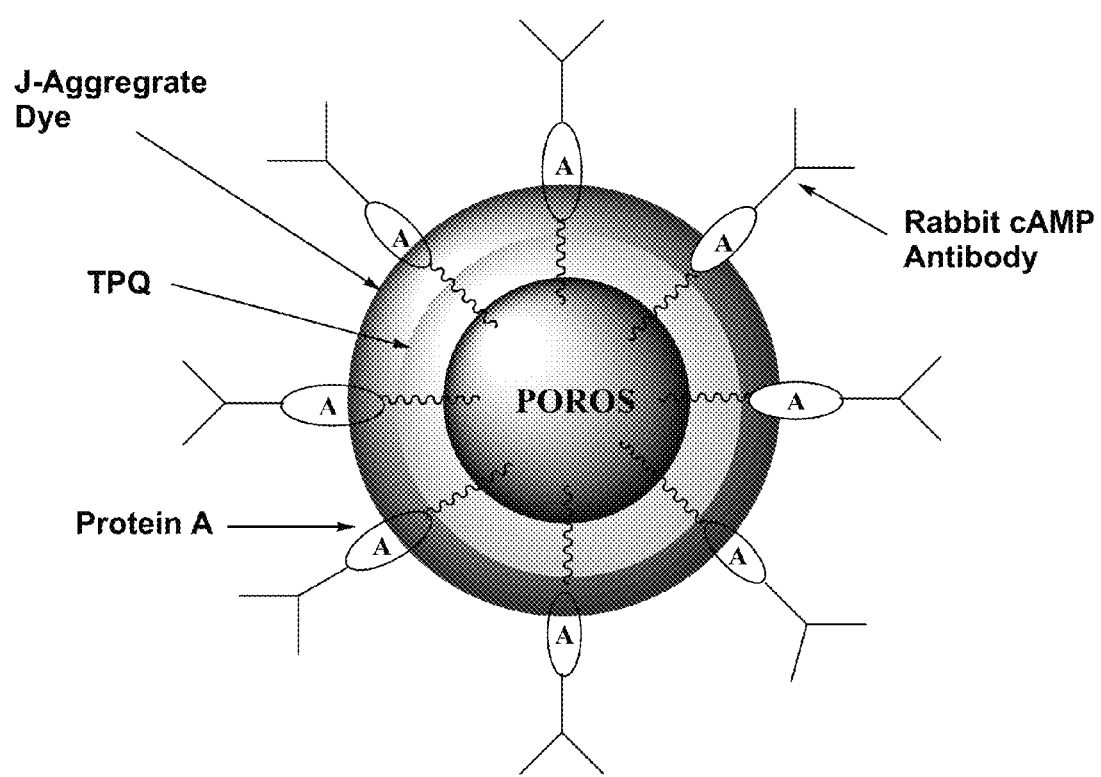
FIG. 2 is a schematic of a construct having a POROS®-A support comprising a chemiluminescent enhancer (i.e., TPQ), a J-aggregate dye and a biomolecular probe (i.e., protein-A) and having Rabbit cAMP antibody bound to the probe.
Figure 3:
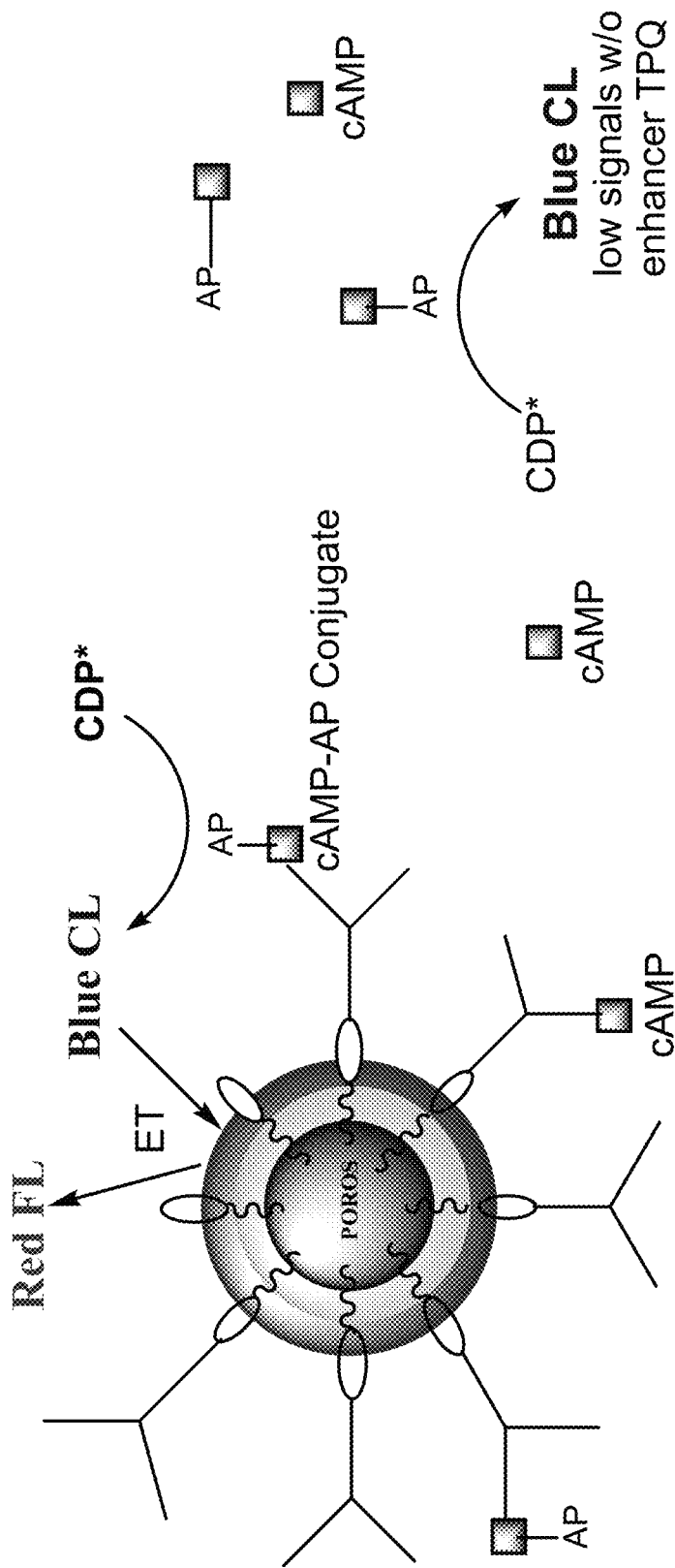
FIG. 3 is a schematic illustrating a competitive assay using the construct of FIG. 2 wherein alkaline phosphatase labeled cAMP added to the sample competes with cAMP in the sample for binding to the Rabbit cAMP antibody bound to the Protein A biomolecular probe on the support surface.

A J-aggregate support construct was used to provide a support for a competitive homogeneous assay of cAMP. cAMP antibody was layered onto a POROS®-A/TPQ/J-aggregate construct as shown in FIG. 2. The POROS®-A surface was coated with TPQ enhancer and J-aggregated cyanine dye. The analyte (cAMP) and a cAMP-alkaline phosphatase conjugate added to the sample competed for capture by the cAMP antibody as shown in FIG. 3. The cAMP-alkaline phosphatase competition with cAMP analyte was detected based on proximity of signal generation (e.g., chemiexcitation of the J-aggregate coating by an excited state dioxetane fragment) occurring near or on the J-aggregate coated surface.

Figure 4:
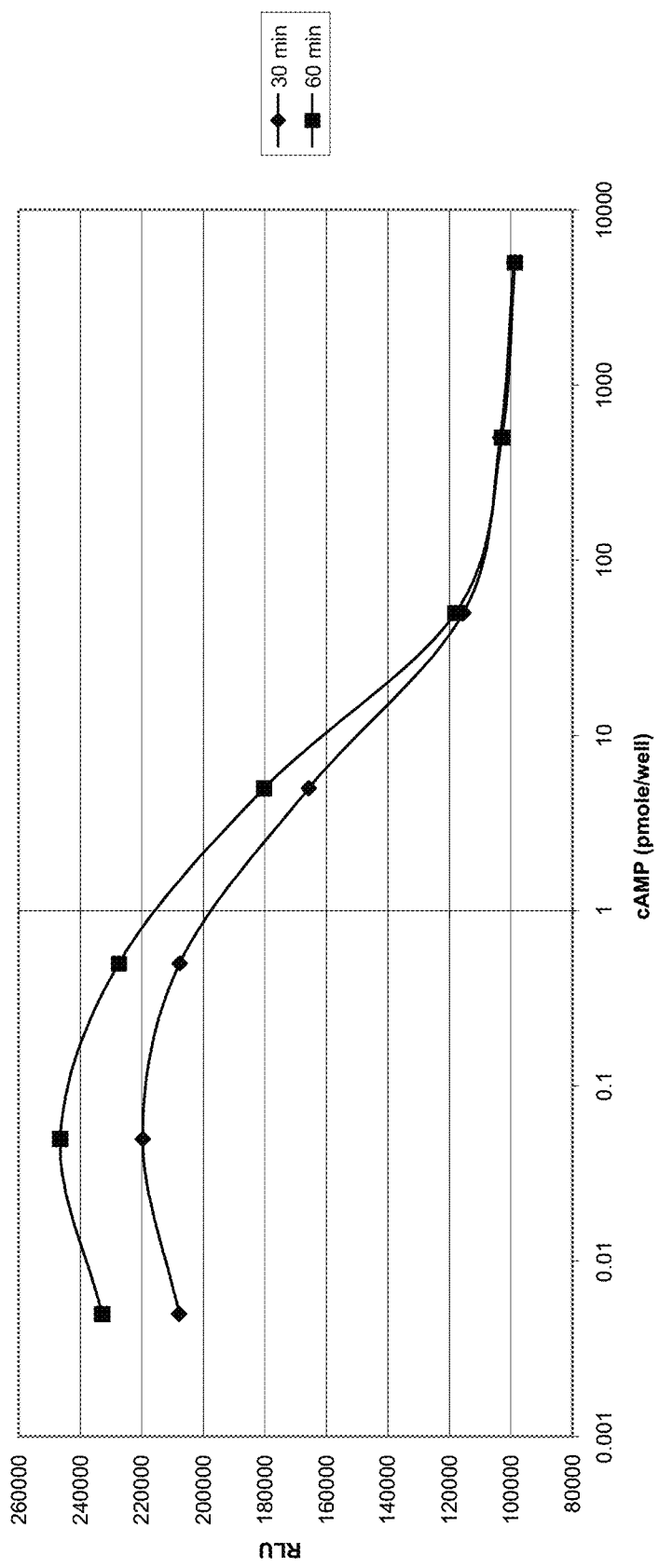
FIG. 4 is a graph showing standard curves for the homogeneous cAMP assay depicted in FIG. 3 using 40 µl cAMP antibody on the POROS® construct and cAMP-alkaline phosphatase conjugate in a 1:50 dilution.

As can be seen from FIG. 3, the blue 460 nm dioxetane CDP-Star® excitation, generated by surface captured alkaline phosphatase, underwent surface TPQ enhancement and energy transfer to produce J-aggregate emission at approximately 600 nm with a narrow emission bandwidth. Any blue chemiluminescent signal (460 nm max), arising from inefficient energy transfer, was minimized due to the lack of polymeric enhancement in the aqueous phase. cAMP analyte was detected over 3 orders of magnitude, from 0.1-100 picomole/well as shown in FIG. 4 which is a graph showing homogeneous cAMP assay standard curves using 40 µl cAMP antibody on the POROS® construct and cAMP-alkaline phosphatase conjugate in a 1:50 dilution.

Figure 5:
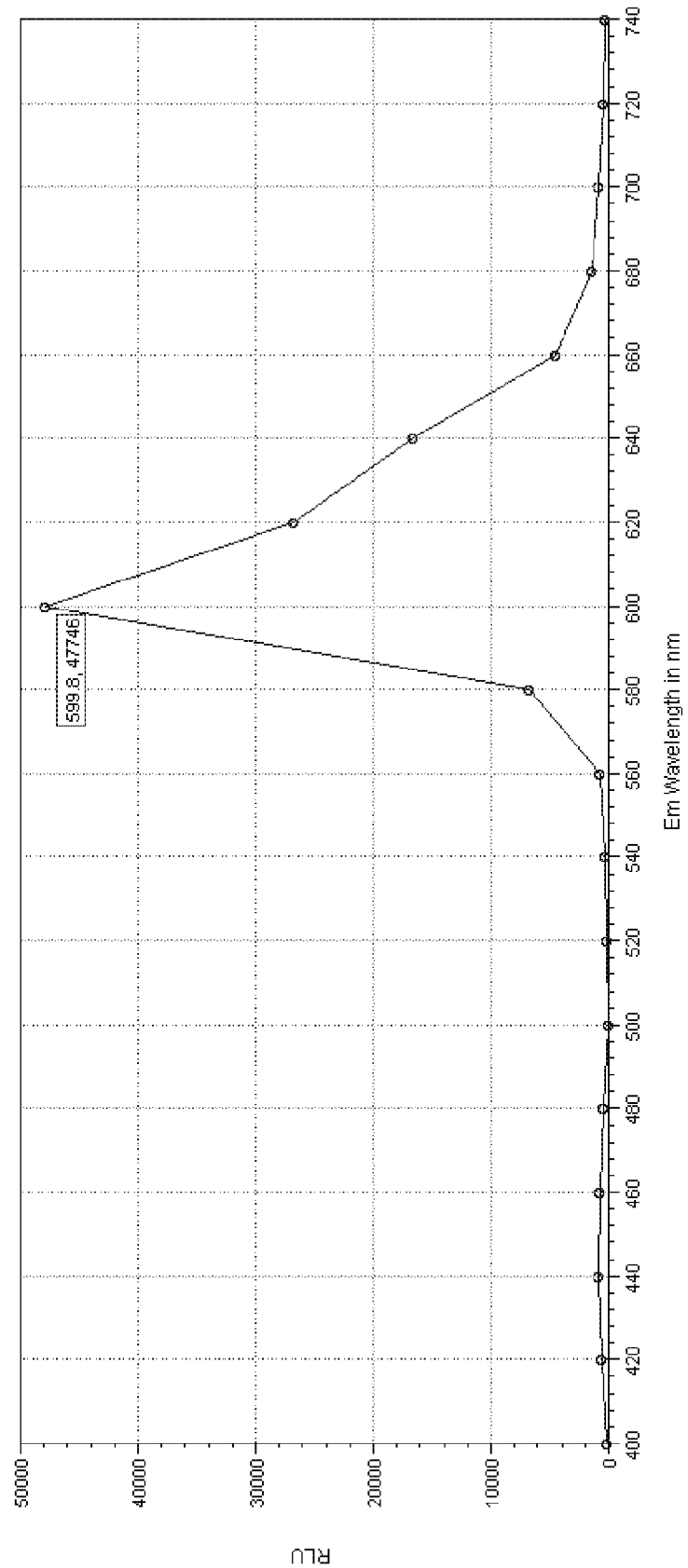
FIG. 5 is a energy transfer (ET) spectrum for the homogeneous cAMP-AP assay using the construct of FIG. 2.

FIG. 5 is an energy transfer (ET) spectrum for the homogeneous cAMP-AP assay using the construct of FIG. 2. The POROS®-A/cAMP antibody/TPQ/J-aggregate construct was suspended in 240 μl PBS buffer containing 0.1% BSA, and was incubated with 10 μl of cAMP-AP conjugate (excess) at room temperature for 60 min. 20 μL of the resulting slurry was placed in a 96-well microplate and treated with 80 μl of 0.4 mM CDP-Star® solution in AMP buffer at pH 9.5. Spectrum was measured on SpectraMax M2 (Molecular Devices Corp.) after incubation of 30 minutes at 37° C. As can be seen from FIG. 5, the ratio of emission peak heights (red at 600 nm:blue at 460 nm) was greater than 56:1.

Protocol of Homogeneous cAMP Competitive Assay

A. cAMP Construct Preparation

1. Pipette 0.3 ml (50 mg) of POROS®-20A slurry and suspend in 0.7 ml of PBS.
2. Centrifuge and discard supernatant.
3. Wash beads in 1 ml of PBS 4 times.
4. Suspend beads in 1 ml of PBS and add 40 μl of rabbit cAMP antibody.
5. Incubate 60 minutes on a plate shaker.
6. Discard supernatant and wash beads sequentially in 1 ml of PBS 5 times and 1 ml of $H_2O$ once.
7. Suspend beads in 1 ml of TPQ stock solution (2 mg/ml $H_2O$).
8. Incubate 60 minutes on a plate shaker.
9. Discard supernatant and wash beads sequentially in 1 ml each of water and 20% MeOH/$H_2O$.
10. Suspend beads in 20% MeOH/$H_2O$ and add 30 μl of dye stock solution (100 mg/2 ml MeOH).
11. Wrap in aluminum foil and incubate 60 minutes on a plate shaker.
12. Discard orange supernatant which forms pink emulsion in aqueous solution.
13. Wash pink color beads sequentially in 1 ml of $H_2O$, 1 ml of BSA/PBS 3 times and 1 ml of Tris buffer (pH=7.0) twice.
14. Suspend the final beads in 1 ml of Tris buffer and store in dark in refrigerator.

B. cAMP Competitive Assay

1. Add 50 μl/well of a series of 1:10 dilutions of cAMP standard solution and 25 μl/well of diluted cAMP-AP conjugate to wells of a 96-microtiter plate and mix on a plate shaker for 10 minutes.
2. Add 5 μl/well of POROS® cAMP construct.
3. Incubate for 60 minutes on a plate shaker.
4. Add 60 μl of 0.4 mM CDP-Star® and mix on a plate shaker for 10 minutes.
5. Place plate in luminometer TR 717 at 29° C. and measure signal after 20 and 50 minutes.

Figure 6:
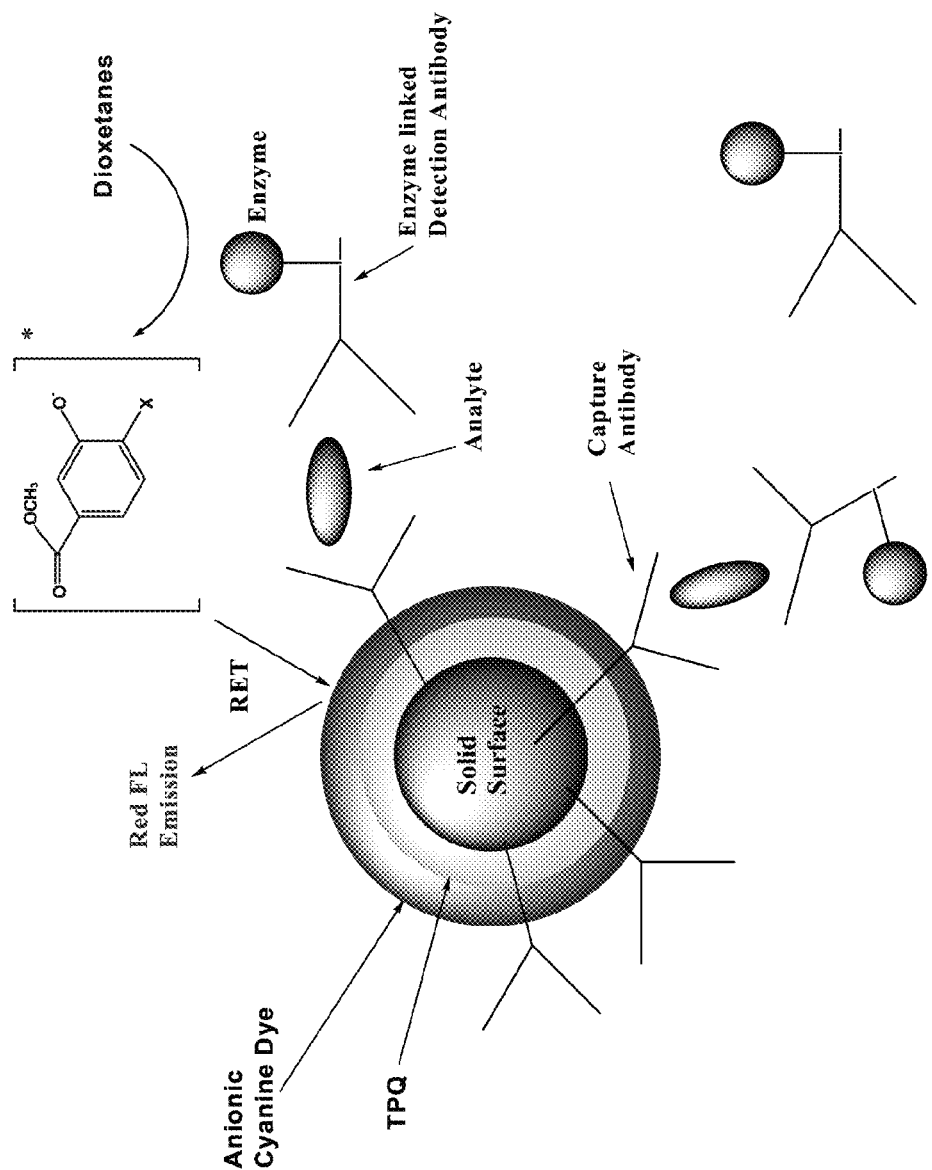
FIG. 6 is a schematic illustrating a sandwich assay using a support comprising a surface, a chemiluminescent enhancer (i.e., TPQ), an anionic cyanine dye (e.g. a J-aggregate dye), a biomolecular probe (i.e., a capture antibody) to capture analyte in the sample and an enzyme-labeled antibody that is capable of binding to the support bound analyte.

FIG. 6 is a schematic illustrating a sandwich assay using a support comprising a surface, a chemiluminescent enhancer (i.e., TPQ), an anionic cyanine dye (e.g. a J-aggregate dye), a biomolecular probe (i.e., a capture antibody) to capture analyte in the sample and an enzyme-labeled antibody that is capable of binding to the support bound analyte. As illustrated in FIG. 6, enzymatic turnover of the dioxetane substrate generates activated chemiluminescent substrate which breaks down to generate light which, through energy transfer (ET), results in fluorescence from the cyanine dye.

FIG. 7 is a schematic depicting a multiplexed, homogeneous sandwich assay. As shown in FIG. 7, activation of a chemiluminescent donor by a first enzyme (Enzyme 1) which is bound to a first support via captured first analyte (Analyte 1) produces a chemiexcited donor which, through energy transfer, results in fluorescence from a first dye (Dye 1) on the surface of the first support. As also shown in FIG. 7, activation of a chemiluminescent donor by a second enzyme (Enzyme 2) which is bound to a second support via captured second analyte (Analyte 2) produces a chemiexcited donor which, through energy transfer, results in fluorescence from a second dye (Dye 2) on the surface of the second support. The fluorescent emissions from the second dye can be distinguished from the emissions from the first dye. Multiple analytes in a sample can therefore be detected either simultaneously or sequentially.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. An article of manufacture comprising;
   a support comprising a surface;
   a chemiluminescent enhancing material on the surface of the support;
   an energy acceptor dye on the surface of the support;
   one or more biomolecular probes on the surface of the support; and
   a molecular filter on the surface of the support;
   wherein the molecular filter is selected from the group consisting of hemoglobin, dabcyl, DPX and DNP C2 Amine and wherein the energy acceptor dye is a J-aggregated dye.

2. The article of claim 1, wherein the molecular filter is hemoglobin.

3. The article of claim 1, wherein the chemiluminescent enhancing material is a cationic homopolymer or copolymer comprising positively charged onium groups.

4. The article of claim 3, wherein the chemiluminescent enhancing material comprises poly(vinylbenzyldimethylbenzylammonium chloride) (BDMQ), poly(vinylbenzyltrimethylammonium chloride) (TMQ), poly(vinylbenzyltributylammonium chloride) (TBQ), poly(vinylbenzyltri(n-pentyl) ammonium chloride) (TPQ), poly(vinylbenzyltributylphosphonium chloride) (TB), poly(vinylbenzyltrioctylphosphonium chloride) (TO), two or more of any of the foregoing or a copolymer comprising one or more of the foregoing.

5. The article of claim 1, wherein the support is a particle.

6. The article of claim 1, wherein the support comprises latex, polystyrene, nylon, polyacrylamide or poly(styrenedivinyl benzene) beads.

7. The article of claim 1, wherein the J-aggregated dye is a cyanine dye.

8. The article of claim 1, wherein the one or more biomolecular probes comprise antibodies, polynucleotide, oligonucleotides, polypeptides, proteins, receptors, lectins or aptamers.

9. The article of claim 1, wherein the support has an anionic surface, the chemiluminescent enhancing material is a cationic homopolymer or copolymer on the support surface and the J-aggregated dye is an anionic dye on the cationic homopolymer or copolymer.

10. The article of claim 9, wherein the anionic dye is an anionic cyanine dye having the structure as set forth below:

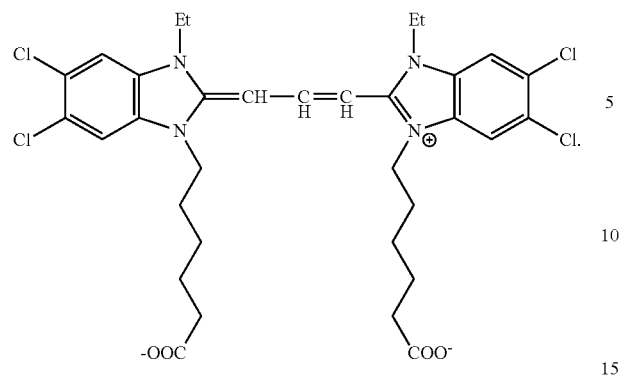
* * * * *